US00PP24867P2

(12) United States Plant Patent
Nishikawa

(10) Patent No.: US PP24,867 P2
(45) Date of Patent: Sep. 9, 2014

(54) ***BIDENS* PLANT NAMED 'FLORBIKANRE'**

(50) Latin Name: *Bidens triplinervia*
Varietal Denomination: Florbikanre

(76) Inventor: Koichiro Nishikawa, Okayama-ken (JP)

( * ) Notice: Subject to any disclaimer, the term of this patent is extended or adjusted under 35 U.S.C. 154(b) by 52 days.

(21) Appl. No.: 13/507,791

(22) Filed: Jul. 27, 2012

(51) Int. Cl.
*A01H 5/00* (2006.01)

(52) U.S. Cl.
USPC ..... Plt./410

(58) Field of Classification Search
USPC ..... Plt./410
See application file for complete search history.

*Primary Examiner* — Annette Para
(74) *Attorney, Agent, or Firm* — C. A. Whealy

(57) ABSTRACT

A new and distinct cultivar of *Bidens* plant named 'Florbikanre', characterized by its large, upright, outwardly spreading to somewhat trailing and mounding plant habit; vigorous growth habit; freely branching habit; freely flowering habit; long flowering period; inflorescences with light red-colored ray florets and yellow-colored disc florets; and strong peduncles that hold the inflorescences above and beyond the foliar plane.

2 Drawing Sheets

Botanical designation: *Bidens triplinervia.*
Cultivar denomination: 'FLORBIKANRE'.

BACKGROUND OF THE INVENTION

The present invention relates to a new and distinct cultivar of *Bidens* plant, botanically known as *Bidens triplinervia* and hereinafter referred to by the name 'Florbikanre'.

The new *Bidens* plant is a product of a planned breeding program conducted by the Inventor in Okayama-ken, Japan. The objective of the breeding program is to create new freely branching *Bidens* plants with unique ray floret coloration.

The new *Bidens* plant originated from a self-pollination made by the Inventor in Okayama-ken, Japan in January, 2010 of *Bidens triplinervia* 'KR-SAIKA001', not patented. The new *Bidens* plant was discovered and selected by the Inventor as a single flowering plant from within the progeny of the stated self-pollination in a controlled greenhouse environment in Okayama-ken, Japan in May, 2010.

Asexual reproduction of the new *Bidens* plant by vegetative cuttings in a controlled environment in Okayama-ken, Japan since June, 2010 has shown that the unique features of this new *Bidens* plant are stable and reproduced true to type in successive generations.

SUMMARY OF THE INVENTION

Plants of the new *Bidens* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Florbikanre'. These characteristics in combination distinguish 'Florbikanre' as a new and distinct *Bidens* plant:

1. Large, upright, outwardly spreading to somewhat trailing and mounding plant habit.
2. Vigorous growth habit.
3. Freely branching habit.
4. Freely flowering habit.

5. Long flowering period.
6. Inflorescences with light red-colored ray florets and yellow-colored disc florets.
7. Strong peduncles that hold the inflorescences above and beyond the foliar plane.

Plants of the new *Bidens* differ primarily from plants of the parent, 'KR-SAIKA001' in ray floret color as inflorescences of the new *Bidens* have light red-colored ray florets whereas inflorescences of 'KR-SAIKA001' have subdued red-colored ray florets.

Plants of the new *Bidens* can be compared to plants of *Bidens triplinervia* 'Florbikano', disclosed in U.S. Plant patent application Ser. No. 13/507,488. In side-by-side comparisons conducted in Okayama-ken, Japan, plants of the new *Bidens* differed from plants of 'Florbikano' in the following characteristics:

1. Plants of the new *Bidens* were taller than plants of 'Florbikano'.
2. Plants of the new *Bidens* had longer and thicker lateral branches than plants of 'Florbikano'.
3. Plants of the new *Bidens* had longer leaves than plants of 'Florbikano'.
4. Plants of the new *Bidens* and 'Florbikano' differed in ray floret color as plants of 'Florbikano' had yellow orange and dark orange bi-colored ray florets.
5. Plants of the new *Bidens* had longer peduncles than plants of 'Florbikano'.

BRIEF DESCRIPTION OF THE PHOTOGRAPHS

The accompanying photographs illustrate the overall appearance of the new *Bidens* plant showing the colors as true as it is reasonably possible to obtain in colored reproductions of this type. Colors in the photographs may differ slightly from the color values cited in the detailed botanical description which accurately describe the colors of the new *Bidens* plant.

The photograph on the first sheet comprises a side perspective view of a typical flowering plant of 'Florbikanre' grown in a container.

The photograph on the second sheet is a close-up view of typical developing (left), fully developed (center) and fading (right) inflorescences of 'Florbikanre'.

DETAILED BOTANICAL DESCRIPTION

The aforementioned photographs and following observations and measurements describe plants grown in 40-cm containers during the late spring in a polyethylene-covered greenhouse in Okayama-ken, Japan and under cultural practices which approximate those generally used in commercial *Bidens* production. During the production of the plants, day temperatures ranged from 20° C. to 30° C. and night temperatures ranged from 5° C. to 10° C. Plants were one year old when the photographs and description were taken. In the following description, color references are made to The Royal Horticultural Society Colour Chart, 2007 Edition, except where general terms of ordinary dictionary significance are used.

Botanical classification: *Bidens triplinervia* 'Florbikanre'.

Parentage: Self-pollination of *Bidens triplinervia* 'KR-SAIKA001', not patented.

Propagation:

*Type*.—By vegetative cuttings.

*Time to initiate roots, summer*.—About two weeks at temperatures about 20° C. to 30° C.

*Time to initiate roots, winter*.—About three weeks at temperatures about 10° C. to 15° C.

*Time to produce a rooted young plant, summer*.—About three weeks at temperatures about 20° C. to 30° C.

*Time to produce a rooted young plant, winter*.—About four weeks at temperatures about 10° C. to 15° C.

*Root description*.—Fine, fibrous; white in color.

*Rooting habit*.—Freely branching; dense.

Plant description:

*Plant and growth habit*.—Large, upright, outwardly spreading to somewhat trailing and mounding plant habit; vigorous growth habit.

*Branching habit*.—Freely branching habit with lateral branches potentially forming at every node.

*Plant height*.—About 40 cm.

*Plant diameter or spread*.—About 100 cm.

*Lateral branches*.—Length: About 21 cm. Diameter: About 1.3 mm. Internode length: About 11 cm. Strength: Strong, flexible. Texture: Slightly pubescent. Color: Close to 144B tinted with close to N77A.

Foliage description:

*Arrangement*.—Opposite, simple.

*Length*.—About 4 cm.

*Width*.—About 2.3 cm.

*Shape*.—Roughly deltoid; pinnatisect.

*Apex*.—Acute.

*Base*.—Acute.

*Margin*.—Deeply incised; laciniate.

*Texture, upper and lower surfaces*.—Smooth, glabrous.

*Venation pattern*.—Pinnate.

*Color*.—Developing leaves, upper surface: Close to 137B. Developing leaves, lower surface: Close to 138B. Fully expanded leaves, upper surface: Close to N137A; venation, close to 137B. Fully expanded leaves, lower surface: Close to 137C; venation, close to 137A.

*Petioles*.—Length: About 1.2 cm. Diameter: About 0.6 mm. Texture, upper surface: Sparsely pubescent. Texture, lower surface: Smooth, glabrous. Color, upper surface: Close to N77A. Color, lower surface: Close to 146A.

Inflorescence description:

*Appearance*.—Single (daisy) inflorescence form with ray and disc florets; inflorescences positioned above and beyond the foliar plane on strong peduncles; inflorescences face mostly upright to outwardly.

*Flowering habit*.—Freely flowering habit with numerous inflorescences developing per plant.

*Fragrance*.—None detected.

*Natural flowering season*.—Long flowering period, plants flower continuously from spring until the autumn in Japan.

*Inflorescence longevity*.—Inflorescences last about one week on the plant; inflorescences persistent.

*Inflorescence buds*.—Height: About 5 mm. Diameter: About 4 mm. Shape: Ovoid. Color: Close to 151A.

*Inflorescence size*.—Diameter: About 3.6 cm. Depth (height): About 9 mm. Disc diameter: About 4 mm. Receptacle diameter: About 1 cm. Receptacle height: About 3 mm. Receptacle color: Close to 137B.

*Ray florets*.—Length: About 1.8 cm. Width: About 1.1 cm. Shape: Ovate. Apex: Emarginate. Base: Obtuse. Margin: Entire. Texture, upper and lower surfaces: Smooth, glabrous. Number of ray florets per inflorescence: Five arranged in a single whorl. Color: When opening, upper surface: Close to 42A. When opening, lower surface: Close to 163A and 169A. Fully opened, upper surface: Close to 42A; towards the base, close to 28A; with development, color becomes closer to 169A and towards the base, close to 163A. Fully opened, lower surface: Close to 163B and N163A; color does not change with development.

*Disc florets*.—Shape: Tubular; apex dentate. Length: About 5 mm. Diameter: About 1 mm. Number of disc florets per inflorescence: About 42. Color, when opening: Towards the apex, close to N167C; towards the base, close to 145B. Color, fully opened: Towards the apex, close to 172A; towards the base, close to 145A.

*Phyllaries*.—Quantity per inflorescence: Seven to eight in a single whorl. Length: About 5 mm. Width: About 0.8 mm. Shape: Lanceolate. Apex: Acute. Base: Truncate. Margin: Entire. Texture, upper and lower surfaces: Smooth, glabrous. Color, upper and lower surfaces: Close to 137B.

*Peduncles*.—Length, terminal peduncle: About 19 cm. Diameter: About 0.9 mm. Strength: Strong; flexible. Aspect: Erect to about 45° from vertical; peduncles holding inflorescences above and beyond the foliar plane. Texture: Smooth, glabrous. Color: Close to 144B tinted with close to N77A.

*Reproductive organs*.—Androecium: Present on disc florets only. Quantity per disc floret: One. Filament length: About 2 mm. Filament color: Close to 145D. Anther shape: Lanceolate. Anther length: About 1.6 mm. Anther color: Close to 200A. Pollen amount: Abundant. Pollen color: Close to 21A. Gynoecium: Present on ray and disc florets. Pistil length: About 6.5 mm. Style length: About 4 mm. Style color: Close to 153D. Stigma shape: Bi-parted. Stigma color: Close to 15A. Ovary color: Close to 145D.

*Seeds and fruits*.—Seed and fruit development have not been observed on plants of the new *Bidens*.

Disease & pest resistance: Plants of the new *Bidens* have not been shown to be resistant to pathogens and pests common to *Bidens* plants.

Garden performance: Plants of the new *Clematis* have exhibited good tolerance to rain and wind and have been observed to tolerate temperatures from about 1° C. to about 47° C.

It is claimed:

1. A new and distinct *Bidens* plant named 'Florbikanre' as illustrated and described.

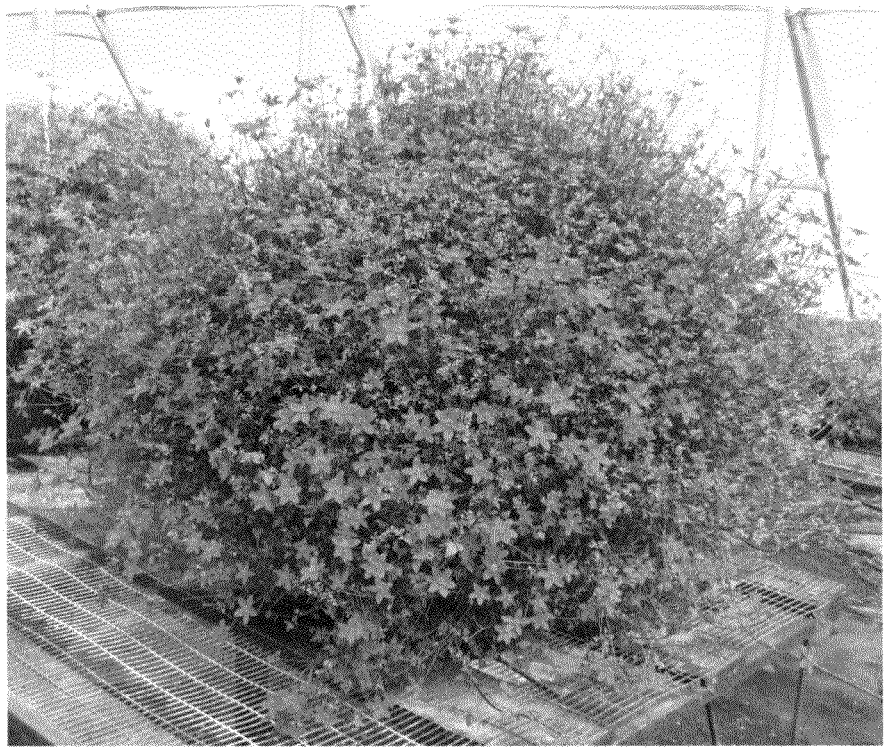

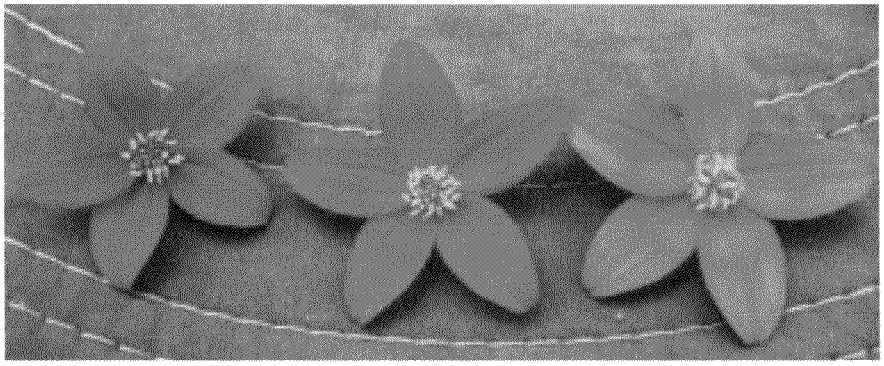

* * * * *